(12) United States Patent
Zisman (10) Patent No.: US 8,410,173 B2
(45) Date of Patent: Apr. 2, 2013

(54) INHIBITION OF JAK2 AS A TREATMENT OF PULMONARY ARTERIAL HYPERTENSION

(75) Inventor: Lawrence S. Zisman, Slingerlands, NY (US)

(73) Assignee: YM Biosciences Australia Pty Ltd, Melbourne, Victoria (AU)

( * ) Notice: Subject to any disclaimer, the term of this patent is extended or adjusted under 35 U.S.C. 154(b) by 522 days.

(21) Appl. No.: 12/280,327

(22) PCT Filed: Feb. 28, 2007

(86) PCT No.: PCT/US2007/062932
§ 371 (c)(1),
(2), (4) Date: Dec. 8, 2010

(87) PCT Pub. No.: WO2007/101232
PCT Pub. Date: Sep. 7, 2007

(65) Prior Publication Data
US 2011/0117159 A1     May 19, 2011

Related U.S. Application Data

(60) Provisional application No. 60/778,009, filed on Feb. 28, 2006.

(51) Int. Cl.
*A61K 31/165*     (2006.01)
(52) U.S. Cl. ........................................ 514/619
(58) Field of Classification Search .................. 514/619
See application file for complete search history.

(56) References Cited

U.S. PATENT DOCUMENTS

| | | | | |
|---|---|---|---|---|
| 5,823,180 | A | * | 10/1998 | Zapol ........................ 128/200.24 |
| 6,379,691 | B1 | * | 4/2002 | Tedeschi et al. ............... 424/423 |
| 6,433,018 | B1 | | 8/2002 | Siddiqui et al. |
| 7,235,588 | B2 | | 6/2007 | Siddiqui et al. |
| 2004/0266661 | A1 | * | 12/2004 | Siddiqui et al. .................... 514/2 |
| 2006/0270694 | A1 | * | 11/2006 | Wong ............................ 514/275 |

OTHER PUBLICATIONS

Provencher et al., Treatment of pulmonary arterial hypertension with bosentan: from pathophysiology to clinical evidence, 2005, Expert Opinion Pharmacotherapy, vol. 6 issue 8, pp. 1337-1348.*
Abe et al., Circ Res (2004) 94:385-393.
Aguilar and Farber, Am J Respir Crit Care Med (2000) 162:1846-1850.
Archer et al., Am J Respir Crit Care Med (1998) 158:1061-1067.
Badesch et al., Ann Intern Med (2000) 132:425-434.
Badesch et al., Chest (2004) 126:35S-62S.
Barst et al., N Engl J Med (1996) 334:296-301.
Deng et al., Am J Hum Genet (2000) 67:737-744.
Galie et al., J Am Coll Cardiol (2005) 46:529-535.
Galie et al., Eur Respir J (2002) 20:1037-1049.
Hill et al., J Appl Physiol (1997) 83:1209-1215.
Hoeper et al., Ann Intern Med (1999) 130:506-509.
Hoeper et al., Eur Respir J (2005) 25:502-508.
Humbert et al., Eur Respir J (1999) 13:1351-1356.
International Preliminary Report on Patentability for PCT/US2007/062932, issued on Oct. 14, 2008, 4 pages.
International Search Report for PCT/US2007/062932, mailed on Sep. 19, 2008, 1 page.
Itoh et al., Am J Respir Crit Care Med (2004) 169:34-38.
Jasmin et al., Circulation (2001) 103:314-318.
Jones et al., Mol Pharm (1995) 48:890-896.
Kataoka et al., Circ J (2005) 69:461-465.
Lane et al., Nature Genetics (2000) 26:81-84.
Langleben et al., J Cardiovasc Pharmacol (2004) 44:S80-S84.9.
Lee et al., Ann Pharmacother (2005) 39:869-884.
Lu et al., J Thorac Cardiovasc Surg (2004) 128:850-859.
Matthew et al., Circulation (2004) 110:1499-1506.
McGoon et al., Chest (2004) 126:14S-34S.
McLaughlin and Rich, Curr Probl Cardiol (2004) 29:575-634.
McLaughlin et al., Circulation (2002) 106:1477-1482.
McLaughlin et al., N Engl J Med (1998) 338:273-277.
Nagaya et al., Heart (2002) 87:340-345.
Oudiz et al., Chest (2004) 126:420-427.
Packer, Ann Intern Med (1985) 103:258-270.
Prie et al., Circulation (1998) 97:2169-2174.
Prie et al., J Pharmacol Exp Ther (1997) 282:1312-1318.
Reeve et al., Am J Physiol Lung Cell Mol Physiol (1999) L213-L219.
Rich et al., N Engl J Med (1992) 327:76-81.
Robbins et al., Chest (2000) 117:14-18.
Rosenzweig et al., Circulation (1999) 99:1858-1865.
Rubin et al., N Engl J Med (2002) 346:896-903.
Schermuly et al., Circ Res (2004) 94:1101-1108.
Schermuly et al., J Clin Invest (2005) 115:2811-2821.
Vachiery and Naeije, Expert Rev Cardiovasc Ther (2004) 2:183-191.
Wang et al., Cell Biology Intl (2005) 29:598-603.
Yuyama et al., Eur J Pharmacol (2004) 496:129-139.

* cited by examiner

*Primary Examiner* — Ali Soroush
(74) *Attorney, Agent, or Firm* — Morrison & Foerster LLP (57) ABSTRACT

The present invention relates to a method of treating pulmonary arterial hypertension by administering a therapeutically effective amount of a selective JAK2 inhibitor to a patient in need thereof.

20 Claims, 3 Drawing Sheets

INHIBITION OF JAK2 AS A TREATMENT OF PULMONARY ARTERIAL HYPERTENSION

CROSS-REFERENCE TO RELATED APPLICATIONS

This application is the national phase of PCT application PCT/US2007/062932 having an international filing date of 28 Feb. 2007, which claims benefit of U.S. Provisional Application Ser. No. 60/778,009 filed 28 Feb. 2006. The contents of the above patent applications are incorporated by reference herein in their entirety.

FIELD OF THE INVENTION

The present invention relates to the use of a JAK2 inhibitor to treat pulmonary arterial hypertension.

BACKGROUND OF THE INVENTION

Pulmonary arterial hypertension (PAH) is defined as pulmonary vascular disease affecting the pulmonary arterioles resulting in an elevation in pulmonary artery pressure and pulmonary vascular resistance but with normal or only mildly elevated left-sided filling pressures (1). PAH is caused by a constellation of diseases that affect the pulmonary vasculature. PAH can be caused by or associated with collagen vascular disorders such as systemic sclerosis (scleroderma), uncorrected congenital heart disease, liver disease, portal hypertension, HIV infection, Hepatitis C, certain toxins, splenectomy, hereditary hemorrhagic teleangiectasia, and primary genetic abnormalities. In particular, a mutation in the bone morphogenetic protein type 2 receptor (a TGF-b receptor) has been identified as a cause of familial primary pulmonary hypertension (PPH)(2, 3). It is estimated that 6% of cases of PPH are familial, and that the rest are "sporadic." The incidence of PPH is estimated to be approximately 1 case per 1 million population. Secondary causes of PAH have a much higher incidence. The pathologic signature of PAH is the plexiform lesion of the lung which consists of obliterative endothelial cell proliferation and vascular smooth muscle cell hypertrophy in small precapillary pulmonary arterioles. PAH is a progressive disease associated with a high mortality. Patients with PAH may develop right ventricular (RV) failure. The extent of RH failure predicts outcome (4).

The evaluation and diagnosis of PAH is reviewed by McLaughlin and Rich (1) and McGoon et al (5). A clinical history, such as symptoms of shortness of breath, a family history of PAH, presence of risk factors, and findings on physical examination, chest x-ray and electrocardiogram may lead to the suspicion of PAH. The next step in the evaluation will usually include an echocardiogram. The echocardiogram can be used to estimate the pulmonary artery pressure from the Doppler analysis of the tricuspid regurgitation jet. The echocardiogram can also be used to evaluate function of the right ventricle and left ventricle, and the presence of valvular heart disease such as mitral stenosis and aortic stenosis. The echocardiogram can also be useful in diagnosing congenital heart disease such as an uncorrected atrial septal defect or patent ductus arteriosus. Findings on echocardiogram consistent with a diagnosis of PAH would include: 1) Doppler evidence for elevated pulmonary artery pressure; 2) right atrial enlargement; 3) right ventricular enlargement and/or hypertrophy; 4) absence of mitral stenosis, pulmonic stenosis, and aortic stenosis; 5) normal size or small left ventricle; 6) relative preservation of or normal left ventricular function. To confirm the diagnosis of PAH a cardiac catheterization to directly measure the pressures on the right side of the heart and in the pulmonary vasculature is mandatory. An accurate measurement of the pulmonary capillary wedge pressure (PCWP) which gives an accurate estimate of the left atrial and left ventricular end-diastolic pressure is also required. If an accurate PCWP cannot be obtained then direct measurement of LV end-diastolic pressure by left heart catheterization is advised. By definition, patients with PAH should have a low or normal PCWP. However, in the late stages of PAH the PCWP can become somewhat elevated though usually not greater than 16 mm Hg (1, 5). The upper limit of normal for mean pulmonary artery pressure in an adult human is 19 mm Hg. A commonly used definition of mean pulmonary artery pressure is one-third the value of the systolic pulmonary artery pressure plus two-thirds of the diastolic pulmonary artery pressure. Severe PAH may be defined as a mean pulmonary artery pressure greater than or equal to 25 mm Hg with a PCWP less than or equal to 15-16 mm Hg, and a pulmonary vascular resistance (PVR) greater than or equal to 240 dynes sec/cm$^5$. Pulmonary vascular resistance is defined as the mean pulmonary artery pressure minus the PCWP divided by the cardiac output. This ratio is multiplied by 80 to express the result in dyne-secs/cm$^5$. The PVR may also be expressed in millimeters Hg per liter per minute which is referred to as Wood Units. The PVR in a normal adult is 67±23 dyne sec/cm$^5$5 or 1 Wood Unit (1, 5, 6). In clinical trials to test efficacy of drugs for PAH, patients with left sided myocardial disease or valvular heart disease are typically excluded (6).

Until recently, the only effective long-term therapy for PAH in conjunction with anticoagulant therapy was continuous intravenous administration of prostacyclin, also known as epoprostenol (PGI2) (7, 8). Recently, the non-selective endothelin receptor antagonist, bosentan, has shown efficacy for the treatment of PAH (9). As the first orally bioavailable agent with efficacy in the treatment of PAH, bosentan represents a significant advance. However, a subset of patients treated with bosentan may continue to deteriorate and require the addition of PGI2. Conversely some patients on PGI2 can be weaned off this medication with the addition of bosentan. PGI2 has both anti-platelet, inotropic, and vasodilatory properties. Recent evidence suggests that PGI2 may have additional beneficial effects on vascular remodeling (10). In most cases, incremental dosing is needed because of apparent tachyphylaxis/resistance. The mechanism for this resistance is not known. Selective endothelin type A receptor antagonists are currently in development for the treatment of PAH (6, 11). Sildenafil, a phosphodiesterase type V (PDE-V) inhibitor has recently been approved for the treatment of PAH (12, 13). PDE-V inhibition results in an increase in cyclic GMP which leads to vasodilation of the pulmonary vasculature. Treprostinil, an analogue of PGI2, can be administered subcutaneously to appropriately selected patients with PAH (14, 15). In addition, Iloprost, another prostacyclin analogue, can be administered in nebulized form by direct inhalation (16). These agents are used to treat PAH of multiple etiologies, including PAH associated with or caused by familial PAH (primary pulmonary hypertension or PPH), idiopathic PAH, scleroderma, mixed connective tissue disease, systemic lupus erythematosus, HIV infection, toxins such as phentermine/fenfluramine, congenital heart disease, Hepatitis C, liver cirrhosis, chronic thrombo-embolic pulmonary artery hypertension (distal or inoperable), hereditary hemorrhagic teleangiectasia, and splenectomy.

The rat monocrotaline model is a standard and well accepted model of PAH. Improvement in pulmonary arterial hypertension from drug treatment in the rat monocrotaline model is predictive of therapeutic response in humans with PAH. For example, both non-selective and selective ETA/B receptor antagonists have been shown to improve nitric oxide mediated pulmonary vasodilation, significantly reduce pulmonary hypertension and improve survival in rats with monocrotaline induced pulmonary arterial hypertension (17-20). In particular, the non-selective endothelin receptor antagonist bosentan, has been shown to reduce pulmonary hypertension and decrease pulmonary artery thickening in the rat monocrotaline model of PAH (21). Currently the non-selective endothelin receptor antagonist, bosentan is approved by the FDA for the treatment of PAH, and several selective ETA receptor antagonists are in phase III clinical trials for the treatment of PAH in humans. Oral sildenafil, which is FDA approved as a treatment of PAH, when given alone or in combination with beraprost, also showed efficacy in the rat monocrotaline model of PAH (22). The long-acting prostacyclin analogue, iloprost, which is also approved for the treatment of PAH in humans, showed efficacy in the treatment of monocrotaline induced PAH in the rat (23). Therefore, it has been established that the rat monocrotaline model of PAH predicts therapeutic response, efficacy, and utility of agents and drugs for the treatment of PAH of multiple and different etiologies in humans.

In the rat monocrotaline model, the Rho-kinase inhibitor, fasudil, prevented the progression of PAH and improved survival (24). In this study, fasudil decreased pulmonary arterial hypertension, pulmonary vascular lesions, endothelial cell dysfunction, and RV hypertrophy. In another study, specific inhibition of p38 MAP kinase with FR167653 was shown to decrease the progression of PAH in the rat monocrotaline model (25). The PDGF inhibitor, imantinib, decreased RV systolic pressure, and improved survival in the rat monocrotaline model of pulmonary arterial hypertension (26).

The JAK/STAT pathway has recently been implicated in the pathophysiology of PAH. JAKs are kinases which phosphorylate a group of proteins called Signal Transduction and Activators of Transcription or STATs. When phosphorylated, STATs dimerize, translocate to the nucleus and activate expression of genes which lead to proliferation of endothelial cells and smooth muscle cells, and cause hypertrophy of cardiac myocytes. There are three different isoforms of JAK: JAK1, JAK2, and JAK3. Another protein with high homology to JAKs is designated Tyk2. An emerging body of data has shown that the phosphorylation of STAT3, a substrate for JAK2, is increased in animal models of PAH. In the rat monocrotaline model, there was increased phosphorylation of the promitogenic transcription factor STAT3. In this same study pulmonary arterial endothelial cells (PAECs) treated with monocrotaline developed hyperactivation of STAT3 (27). A promitogenic agent or protein is an agent or protein that induces or contributes to the induction of cellular proliferation. Therefore, one effect of JAK2 inhibition would be to decrease proliferation of endothelial cells or other cells, such as smooth muscle cells. A contemplated effect of a JAK2 inhibitor would be to decrease the proliferation of endothelial cells or other cells which obstruct the pulmonary arteriolar lumen. By decreasing the obstructive proliferation of cells, a JAK2 inhibitor could be an effective treatment of PAH.

However, whether or not inhibition of JAK2, and consequent reduction in phosphorylation of STAT3, ameliorates PAH was not previously known. Examples of the use of a JAK2 inhibitor to treat heart failure and systemic hypertension have been reported in PCT/US02/23444 "Method for Reducing Hypertension and Heart Failure." PAH is a substantially different disease than systemic hypertension. PAH is characterized by high pulmonary artery and right ventricular pressures due to increased pulmonary vascular resistance; systemic hypertension is characterized by elevated pressure in the systemic circulation. Typically patients with PAH do not have systemic hypertension. PCT/US02/23444 does not contemplate the use of a selective JAK2 inhibitor as a treatment for PAH.

Because a drug may be effective as a treatment for systemic hypertension does not mean that it will also be effective for treating PAH. For example a vasodilator drug that is effective for treating systemic hypertension, such as the ACE-inhibitor Captopril, can worsen pulmonary arterial hypertension and RV failure in patients with PAH. Evidence for the potential deleterious effect of drugs used to treat systemic hypertension on PAH are given by Packer M, Vasodilator Therapy for Primary Pulmonary Hypertension, Annals of Internal Medicine 1985; 103: 258-270, which is hereby incorporated by reference (28). The one known exception to this limitation is that approximately 15-20% of patients with idiopathic PAH respond to calcium channel blockers, agents which also may be used to treat systemic hypertension. In order to determine if a patient has so-called "reactive" PAH and may be a responder to therapy with a calcium channel blocker, the diagnostic evaluation of PAH includes a pulmonary artery catheterization and acute challenge with adenosine, prostacyclin, or inhaled nitric oxide. If the patient has a greater than 10 mm Hg reduction in the mean pulmonary artery pressure and the mean pulmonary artery pressure decreases to less than or equal to 40 mm Hg with one of these agents, then testing to determine if the patient will respond to a calcium channel blocker may be performed (29, 30). Some clinicians will consider PAH reactive if there is a 20% or greater decrease in the mean pulmonary artery pressure in response to adenosine, prostacyclin, or inhaled nitric oxide. The reason that testing for acute vasoreactivity with protstacyclin, adenosine, or inhaled nitric oxide is performed prior to testing with a calcium channel blocker is that some patients given a calcium channel blocker who were not previously shown to have acute vasoreactivity have died (30). This complicated evaluation and treatment algorithm emphasizes that drugs used to treat systemic hypertension are not necessarily appropriate for patients with PAH.

A JAK2 inhibitor is any compound that selectively inhibits the activity of JAK2. One activity of JAK2 is to phosphorylate a STAT protein. Therefore an example of an effect of a JAK2 inhibitor is to decrease the phosphorylation of one or more STAT proteins. The inhibitor may inhibit the phosphorylated form of JAK2 or the non-phosphorylated form of JAK2. The JAK2 inhibitor may be any type of compound. For example, the compound may be a small organic molecule or a biological compound, such as an antibody or an enzyme.

Examples of JAK2 inhibitors include some members of small organic molecules called tyrphostins. Tyrphostins inhibit the activity of protein tyrosine kinases and have the basic structure shown in structure 1 below:

Structure 1

A preferred class of tyrphostins for use are those compounds represented by Structure 1 wherein:
R1=C$_6$H$_5$—CH$_2$—NH
R2 and R3=H, OH, lower alkyl, F, NO$_2$, CF$_3$, C$_6$H$_5$—SO$_2$, O-R4, O—CO—R4, or R4
R4=phenyl or lower alkyl; and
Lower alkyl=C1-C4 branched or unbranched alkyl (for example, methyl or ethyl).
R2 and R3 may be the same or different except R2 and R3 cannot both be H. Preferably, R2 and R3 are OH.

The tyrphostin may be any tyrphostin that selectively inhibits JAK2. Some examples of tyrphostins include structures described by Meydan et al. (1996) *Nature*, 379:645-648; and Levitzki et al (1995) *Science*, 267:1782-1788, and referred to in application PCT/US02/23444 (International Publication Number WO 03/020202 A2). These structures are incorporated herein by reference.

The preferred compound is known as Tyrphostin AG490, which is a selective, specific, and potent JAK2 protein tyrosine kinase inhibitor. The structure of AG490 is shown as structure 2 below:

Structure 2

A compound is considered a selective inhibitor of JAK2 when the compound inhibits JAK2 activity to an extent significantly greater than it inhibits the activity of other members of the JAK family, i.e., JAK1, JAK3, and Tyk2. Preferably the selective JAK2 inhibitor inhibits JAK2 at least 2-fold more than it inhibits other members of the JAK family, more preferably at least about 5-fold more, and most preferably at least about 10-fold more.

A Symposium sponsored by the World Health Organization (WHO) was held in 1998 which developed a clinical Classification of PAH. McLaughlin V V and Rich S (Current Problems in Cardiology 2004; 29:575-634) summarized the clinical classification of PAH developed at this symposium (1). The present invention contemplates the use of a JAK2 inhibitor to treat the following specific forms of PAH described in the WHO classification of PAH: familial or idiopathic PAH; PAH associated with connective tissue disease; PAH associated with congenital heart disease; PAH associated with portal hypertension; PAH associated with HIV infection; PAH associated with Drugs/toxins; PAH associated with thromboembolic obstruction of the distal pulmonary arteries.

Evidence of the association of PAH with the connective tissue disease scleroderma is given by Badesch et al (31). In this application connective tissue disease and collagen vascular disorder are synonyms. Evidence of the association of PAH with the collagen vascular disorder called "mixed connective tissue disease", Sjogren's syndrome, and/or systemic lupus erythematosus is given by Humbert et al (32). Robbins et al (33) previously reported on the use of epoprostenol to treat PAH associated with systemic lupus erythematosus. Evidence for the association of PAH with HIV infection is given by Aguilar and Farber (34). Evidence for the association of PAH with congenital heart defects is given by Rosenzweig et al (35). Evidence for the association of PAH with fenfluramine, an anorexigen, is given by Archer et al (36). Evidence for the association of PAH with phentermine is given by Reeve et al (37). Evidence for the association of PAH with thromboembolic disease is given by Nagaya et al (38). Evidence for the association of PAH with hereditary hemorrhagic teleangiectasia is given by Mc Goon et al (5). Review of diseases associated with PAH are given by McGoon et al (5) and Badesch et al (30).

The present invention also contemplates the use of a JAK2 inhibitor to treat PAH associated with splenectomy. Evidence for the association of PAH with splenectomy is given by Hoeper et al. (39). Evidence for the association of PAH with portal hypertension is given by Hoeper et al. (40).

DETAILED DESCRIPTION

To test the efficacy of JAK2 inhibition as a treatment for PAH, the rat monocrotaline model of pulmonary arterial hypertension was used. Animals with pulmonary arterial hypertension induced by monocrotaline were treated for three weeks with the selective JAK2 inhibitor, AG490, or vehicle. AG490 is a tyrphostin based tyrosine kinase inhibitor selective for JAK2.

The major findings of this study were that AG490 at a dose of 1 mg/kg tid (three times a day) significantly reduced right ventricular (RV) systolic pressures in monocrotaline treated rats compared to vehicle at day 21. (RV systolic pressure in AG490 treated group: 29.23±4.5 mm Hg vs. 38.44±3.1 mm Hg in the vehicle treated group, a 24% reduction, p=0.023). The RV systolic pressure reflects the pulmonary artery systolic pressure, and it is generally accepted that RV systolic pressure may be used as a surrogate measure of pulmonary artery systolic pressure.

The study design is summarized in Table 1.

TABLE 1

Study design.

| Group ID | # animals | Manipulation |
|---|---|---|
| 1 | 8 | saline control group |
| 2 | 8 | monocrotaline 50 mg/kg × 1 SQ injection and IP, SID (once a day) dose with vehicle only; vehicle given daily through day 21 |
| 3 | 8 | monocrotaline 50 mg/kg × 1 SQ injection and IP, SID dose with AG490 @ 1 mg/kg/day, Dosing of AG490 begins day 1 post monocrotaline and continued daily through day 21 |
| 4 | 8 | monocrotaline 50 mg/kg × 1 SQ injection and IP, SID dose with AG490 @ 3 mg/kg/day, 1st dose AG490 begins day 1 post monocrotaline and continued daily through day 21 |

TABLE 1-continued

Study design.

| Group ID | # animals | Manipulation |
|---|---|---|
| 5 | 8 | monocrotaline SQ injection and IP TID dose w/AG490@ 1 mg/kg/dose (=3 mg/kg/day). AG490 dosing begins day 1 post monocrotaline and continued daily through day 21. |

Figure 1:
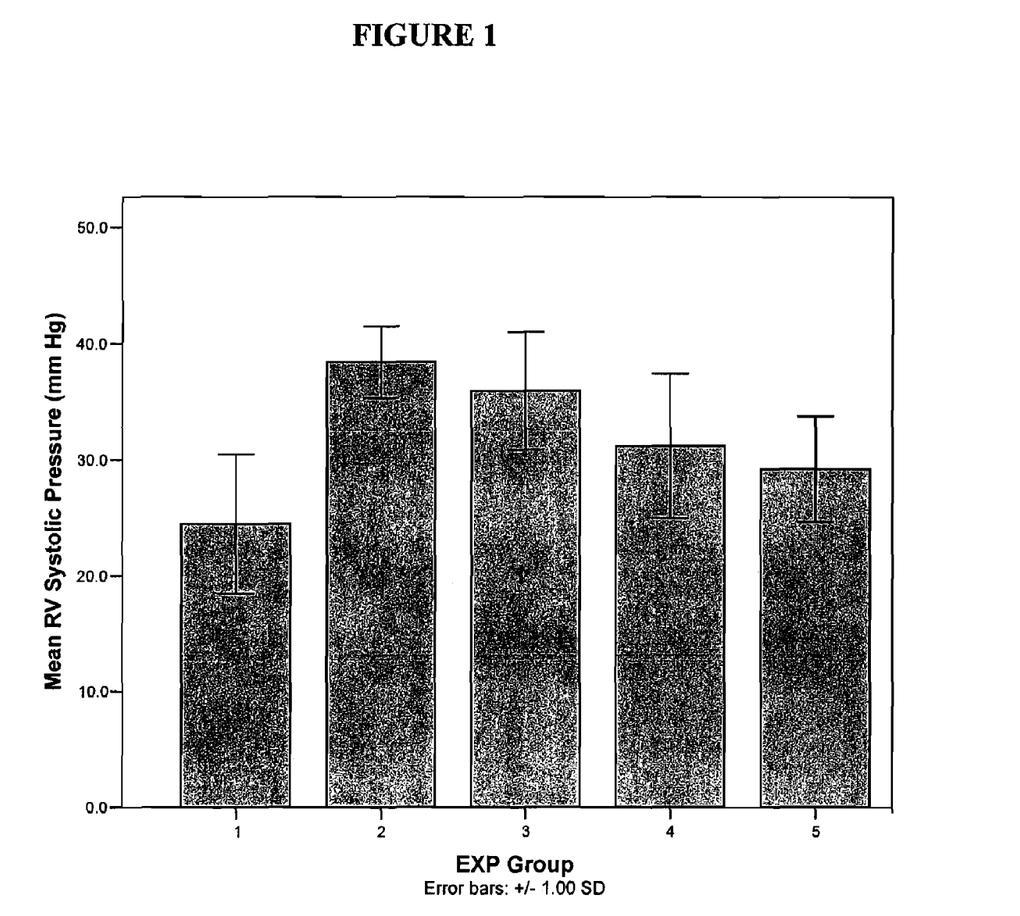
FIG. 1 shows the mean RV systolic pressure +/− one standard deviation for each experimental group in the study summarized in Table 1.

Additionally, FIG. 1 shows the mean RV systolic pressure +/− one standard deviation for each experimental group. There was a significant reduction in RV systolic pressure in group 5 (AG490 1 m/kg tid) compared to group 2 (vehicle only) (p=0.023). Group definitions: 1, non monocrotaline vehicle only controls; 2, monocrotaline, vehicle; 3 monocrotaline, AG490 1 mg/kg/day; 4, monocrotaline, AG490 3 mg/kg once a day; 5, monocrotaline, AG490 1 mg/kg three times a day (tid).

Table 2 shows the results of the statistical analysis for RV systolic pressure. The major finding was that the mean RV systolic pressure was significantly lower in group 5 (AG490 1 mg/kg tid) compared to group 2 (vehicle only). The RV systolic pressure was significantly lower in the saline control group (group 1) compared to the monocrotaline/vehicle group (group 2) demonstrating that monocrotaline caused a significant increase in RV systolic pressure. No improvement in RV systolic pressure was observed in the group treated with only 1 mg/kg/day of AG490 (group 3).

TABLE 2

ANOVA followed by the Bonferroni correction was used to analyze RV systolic pressure. The major finding was that RV systolic pressure (RVS) was lower in group 5 compared to group 2.
Multiple Comparisons
Dependent Variable: RVS
Bonferroni

| (I) EXP Group | (J) EXP Group | Mean Difference (I − J) | Std. Error | Sig. | 95% Confidence Interval | |
|---|---|---|---|---|---|---|
| | | | | | Lower Bound | Upper Bound |
| 1 | 2 | −13.955* | 2.6865 | .000 | −22.074 | −5.836 |
|   | 3 | −11.468* | 2.8034 | .003 | −19.940 | −2.996 |
|   | 4 | −6.730 | 2.5954 | .144 | −14.574 | 1.114 |
|   | 5 | −4.741 | 2.6865 | .875 | −12.860 | 3.378 |
| 2 | 1 | 13.955* | 2.6865 | .000 | 5.836 | 22.074 |
|   | 3 | 2.487 | 2.8879 | 1.000 | −6.240 | 11.215 |
|   | 4 | 7.225 | 2.6865 | .114 | −.894 | 15.344 |
|   | 5 | 9.214* | 2.7746 | .023 | .829 | 17.600 |
| 3 | 1 | 11.468* | 2.8034 | .003 | 2.996 | 19.940 |
|   | 2 | −2.487 | 2.8879 | 1.000 | −11.215 | 6.240 |
|   | 4 | 4.738 | 2.8034 | 1.000 | −3.734 | 13.210 |
|   | 5 | 6.727 | 2.8879 | .265 | −2.001 | 15.455 |
| 4 | 1 | 6.730 | 2.5954 | .144 | −1.114 | 14.574 |
|   | 2 | −7.225 | 2.6865 | .114 | −15.344 | .894 |
|   | 3 | −4.738 | 2.8034 | 1.000 | −13.210 | 3.734 |
|   | 5 | 1.989 | 2.6865 | 1.000 | −6.130 | 10.108 |
| 5 | 1 | 4.741 | 2.6865 | .875 | −3.378 | 12.860 |
|   | 2 | −9.214* | 2.7746 | .023 | −17.600 | −.829 |
|   | 3 | −6.727 | 2.8879 | .265 | −15.455 | 2.001 |
|   | 4 | −1.989 | 2.6865 | 1.000 | −10.108 | 6.130 |

Based on observed means.
*The mean difference is significant at the .05 level.

RV End Diastolic Pressure. Descriptive statistics for RV End Diastolic Pressure are shown in Table 3 and FIG. 2. Statistical analysis of RVEDP demonstrated a significant reduction in group 5 compared to group 2 (Table 4).

TABLE 3

Data summary of RVEDP (mm Hg)

| Exp Group | N | Mean | Std. Deviation | Std. Error | 95% Confidence Interval for Mean | | Minimum | Maximum |
|---|---|---|---|---|---|---|---|---|
| | | | | | Lower Bound | Upper Bound | | |
| 1 | 8 | −1.502 | 4.3556 | 1.5399 | −5.143 | 2.140 | −7.7 | 7.4 |
| 2 | 7 | 4.100 | 3.6375 | 1.3748 | .736 | 7.465 | −.3 | 8.5 |
| 3 | 6 | 4.042 | 3.4361 | 1.4028 | .436 | 7.648 | −1.6 | 7.8 |
| 4 | 8 | −.858 | 3.0055 | 1.0626 | −3.371 | 1.654 | −4.8 | 4.4 |
| 5 | 7 | −1.521 | 2.5733 | .9726 | −3.901 | .859 | −3.8 | 3.1 |
| Total | 36 | .651 | 4.1911 | .6985 | −.767 | 2.069 | −7.7 | 8.5 |

Figure 2:
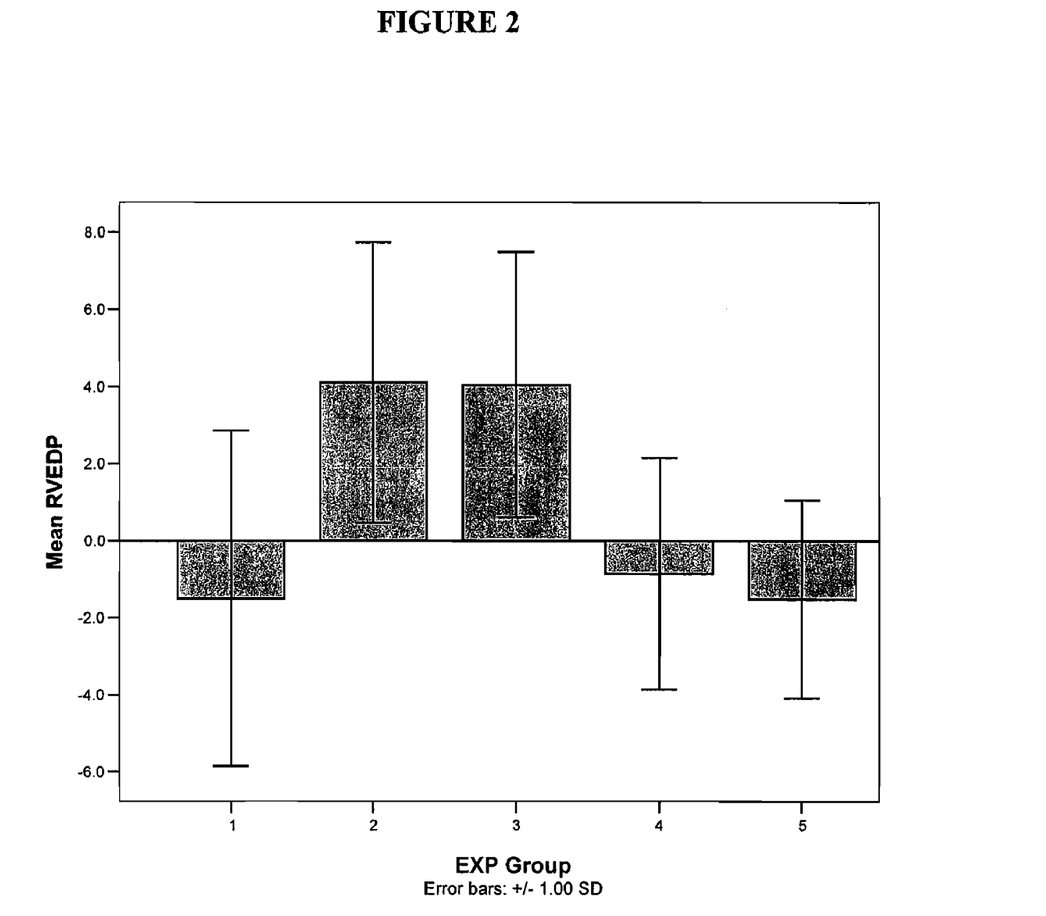
FIG. 2 shows the RV End diastolic pressure (mm Hg) in the study summarized in Table 1.

FIG. 2 shows the RV End diastolic pressure (mm Hg) was significantly lower in group 5 (AG490 1 mg/kg tid) compared to group 2 (vehicle) (p=0.05).

TABLE 4

Summary of ANOVA followed by Bonferroni multiple comparison test for RVEDP data. RVEDP was significantly lower in group 5 compared to group 2.
Multiple Comparisons
Dependent Variable: RVEDP
Bonferroni

| (I) EXP Group | (J) EXP Group | Mean Difference (I − J) | Std. Error | Sig. | 95% Confidence Interval | |
|---|---|---|---|---|---|---|
| | | | | | Lower Bound | Upper Bound |
| 1 | 2 | −5.6021* | 1.7981 | .039 | −11.036 | −.168 |
| | 3 | −5.5436 | 1.8763 | .059 | −11.214 | .127 |
| | 4 | −.6433 | 1.7371 | 1.000 | −5.893 | 4.606 |
| | 5 | .0193 | 1.7981 | 1.000 | −5.415 | 5.453 |
| 2 | 1 | 5.6021* | 1.7981 | .039 | .168 | 11.036 |
| | 3 | .0585 | 1.9329 | 1.000 | −5.783 | 5.900 |
| | 4 | 4.9588 | 1.7981 | .097 | −.475 | 10.393 |
| | 5 | 5.6214* | 1.8571 | .049 | .009 | 11.234 |
| 3 | 1 | 5.5436 | 1.8763 | .059 | −.127 | 11.214 |
| | 2 | −.0585 | 1.9329 | 1.000 | −5.900 | 5.783 |
| | 4 | 4.9003 | 1.8763 | .138 | −.770 | 10.571 |
| | 5 | 5.5629 | 1.9329 | .072 | −.279 | 11.404 |
| 4 | 1 | .6433 | 1.7371 | 1.000 | −4.606 | 5.893 |
| | 2 | −4.9588 | 1.7981 | .097 | −10.393 | .475 |
| | 3 | −4.9003 | 1.8763 | .138 | −10.571 | .770 |
| | 5 | .6626 | 1.7981 | 1.000 | −4.771 | 6.097 |
| 5 | 1 | −.0193 | 1.7981 | 1.000 | −5.453 | 5.415 |
| | 2 | −5.6214* | 1.8571 | .049 | −11.234 | −.009 |
| | 3 | −5.5629 | 1.9329 | .072 | −11.404 | .279 |
| | 4 | −.6626 | 1.7981 | 1.000 | −6.097 | 4.771 |

*The mean difference is significant at the .05 level.

Figure 3:
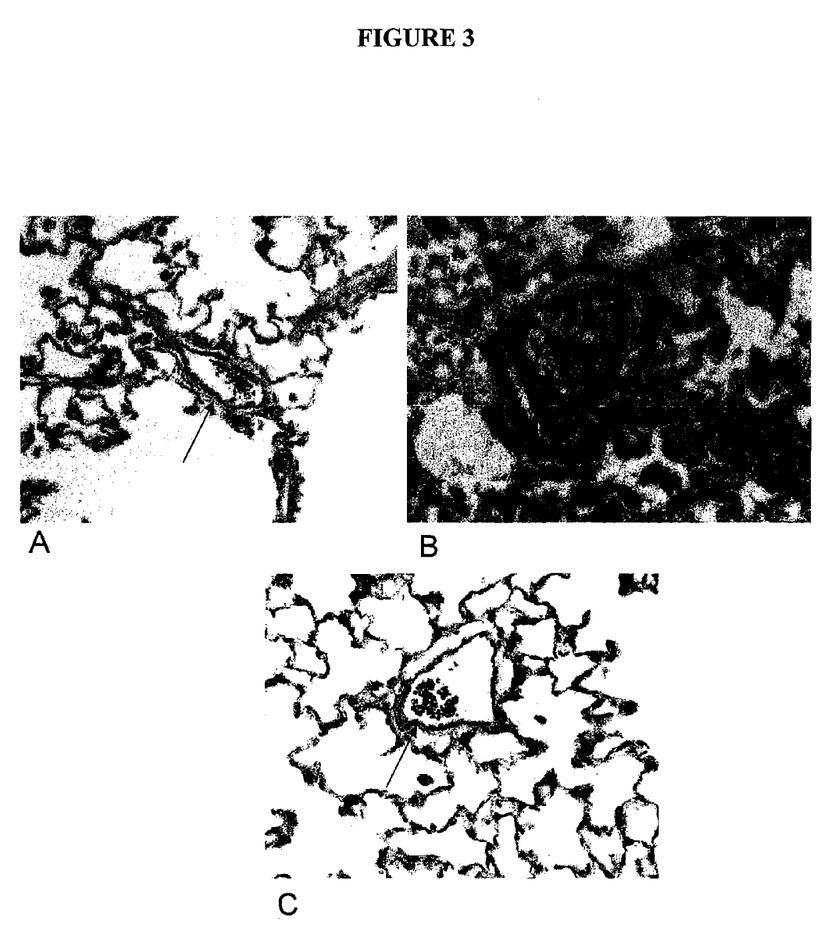
FIG. 3 shows the H&E stains of formalin fixed lungs from rats with pulmonary hypertension induced by monocrotaline demonstrating that selective JAK2 inhibition with AG490 prevented the formation of plexiform lesions which constitute the underlying pathology of PAH. A. Normal lung; B. Lung from monocrotaline treated animal. C. Lung from rat given monocrotaline and AG490 1 mg/kg tid. The arrows point to pulmonary arterioles.

Histological studies of the lungs from group 2 and group 5 were performed to determine the effect of selective JAK2 inhibition on the pulmonary vascular lesions associated with PAH. FIG. 3, demonstrates that AG490 at a dose of 1 mg/kg tid decreased the plexiform lesions associated with pulmonary arterial hypertension.

The use of AG490 as a selective JAK2 inhibitor is meant only as an example. Other selective JAK2 inhibitors which demonstrate selective inhibition of JAK2 compared to JAK3 and/or other kinases are contemplated by these claims. AG490 is a tryphostin based tyrosine kinase inhibitor that is selective for JAK2. However, other chemical entities of a structure different than AG490 and/or in a different class of chemical structures than AG490 which are selective JAK2 inhibitors are contemplated by the present invention. The degree of selectivity may vary. The degree of selectivity of a selective JAK2 inhibitor may be 1 to 2 fold, 2 to 5 fold, 5 to 10 fold, or 10 to 100 fold or greater in its selectivity over JAK3 when measured by the IC50 in vitro or in cell culture.

The present invention also encompasses pharmaceutical compositions containing prodrugs.

Where the compound possesses a chiral centre the compound can be used as a purified isomer or as a mixture of any ratio of isomers. It is however preferred that the mixture comprises at least 70%, 80%, 90%, 95%, or 99% of the preferred isomer.

In a second aspect the present invention comprises a composition comprising a carrier and at least one compound of the first aspect of the present invention.

The present invention provides pharmaceutical compositions comprising at least one compound which is a selective JAK-2 inhibitor in an amount effective therefore, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The selective JAK2 inhibitor may be administered by any suitable means, for example, transdermally; intraperitoneally; orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The selective JAK2 inhibitor may also be administered by inhalation into the lungs by a nebulizer or multi-dose inhaler. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The controlled or extended release formulation may be administered by different routes, including oral, subcutaneous, or by inhalation.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above methods, in whom which JAK2 inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician. In the case of PAH in humans, a medical response to a therapeutically effective amount may include any one or more of the following: 1) An improvement in the six minute walk test by 5-10 meters, 10-20 meters, 20-30 meters, or greater compared to a baseline study prior to initiation of the therapy; 2) an improvement in World Health Organization functional Class from Class IV to Class III, Class IV to Class II, Class IV to Class I, Class III to Class II, Class III to Class I, or Class II to Class I with the former class being the WHO Class prior to initiation of the therapy; 3) a decrease in mean pulmonary artery pressure by 2-4 mm Hg, 4-6 mm Hg, 6-10 mm Hg or greater compared to a baseline study performed prior to initiation of the therapy; 4) an increase in the cardiac index by 0.05-0.1, 0.1-0.2, 0.2-0.4 liter/min/m2 or greater compared to baseline study performed prior to initiation of the therapy; 5) an improvement in PVR (i.e., a decrease) by 25-100, 100-200, 200-300 dysne-sec/cm5 or greater from baseline values obtained prior to initiation of the therapy; 6) a decrease in right atrial pressure by 0.1-0.2, 0.2-0.4, 0.4-1, 1-5 mm Hg or greater compared to a baseline study performed prior to initiation of the therapy; 7) a improvement in survival compared to a group of patients not given the therapy. The time between baseline study prior to initiation of therapy and time of evaluation of efficacy can vary but would typically fall in the range of 4-12 weeks, 12-24 weeks, or 24-52 weeks. Examples of therapeutic efficacy endpoints are given in references 4, 6-9, 11, and 31.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the present invention to the individual in need of treatment.

The pharmaceutical compositions for the administration of the compounds of the present invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The term "pre-capillary pulmonary hypertension" is used herein to indicate pulmonary hypertension that is not caused by elevated left-sided filling pressures in the heart. The term pre-capillary pulmonary hypertension and pulmonary arterial hypertension are used as synonyms in this application.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the present invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical or transdermal use, creams, ointments, jellies, pads, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The present invention also contemplates the use of a selective JAK2 inhibitor contained within or attached to an implant, such as a pulmonary artery stent, which may act locally, or be released from the stent into the pulmonary circulation where the drug may exert its therapeutic activity in the pulmonary vasculature.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include, but are not limited to, the following: Prostacyclin (synonyms: epoprostenol, PGI2), treprostinil, iloprost, beraprost, bosentan (a non-selective endothelin receptor antagonist), Sitaxsentan (a selective endothelin type A receptor antagonist), ambrisentan (a selective endothelin type A receptor antagonist), sildenafil (a PDE-V inhibitor), nitric oxide, oxygen, heparin, warfarin, diuretics, digoxin.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require JAK2 inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. The dosing interval may be once a month, or once a week.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention contemplates the use of a modified selective JAK2 inhibitor which is administered as a pro-drug, but which is metabolized to an active form when administered. The present invention also contemplates the use of a selective JAK2 inhibitor attached by chemical or other means to an inert or biodegradable transport substance such as a nanoparticle, polymer, or carrier protein.

REFERENCES

1) McLaughlin, V. V., and Rich, S. 2004. Pulmonary hypertension. *Curr Probl Cardiol* 29:575-634.

2) The International PPH Consortium. Lane K B, Machado R D, Pauciulo M W, Thomson J R, Philips III J A, Loyd J E, Nichos W C, Trembath R C. 2000. Heterozygous germline mutations in BMPR2, encoding a TGF-b receptor, cause familial primary pulmonary hypertension. *Nature Genetics* 26: 81-84.

3) Deng z, Morse J H, Slager S L, Curevo N, Moore K J, Venetos G, Klachikov S, Cayanis E, Fischer S G, Barst R J, Hodge S E, Knowles J A. 2000. Familial primary pulmonary hypertension (gene PPH1) is caused by mutations in the bone morphogenetic protein receptor-II gene. *Am J Hum Genet.* 67: 737-44.

4) McLaughlin V V, Shillington A, Rich S. 2002. Survival in primary pulmonary hypertension: the impact of epoprostenol therapy. *Circulation* 106: 1477-82.

5) McGoon, M., Gutterman, D., Steen, V., Barst, R., McCrory, D. C., Fortin, T. A., and Loyd, J. E. 2004. Screening, early detection, and diagnosis of pulmonary arterial hypertension: ACCP evidence-based clinical practice guidelines. *Chest* 126:14 S-34S.

6) Galie, N., Badesch, D., Oudiz, R., Simonneau, G., McGoon, M. D., Keogh, A. M., Frost, A. E., Zwicke, D., Naeije, R., Shapiro, S., et al. 2005. Ambrisentan therapy for pulmonary arterial hypertension. *J Am Coll Cardiol* 46:529-535.

7) Barst, R., L. Rubin, W. Long, M. Mcgoon, S. Rich, D. Badesch, B. Groves, V. Tapson, R. Bourge, B. Brundage, S. Koerner, D. Langleben, C. Keller, S. Murali, B. Uretsky, L. Clayton, M. Jobsis, S. Blackburn, D. Shortino, J. Crow, and f. t. P. P. H. S. Group. 1996. A comparison of continuous intravenous epoprostenol (prostacyclin) with conventional therapy for primary pulmonary hypertension. *N Engl J Med* 334:296-301.

8) McLaughlin, V., D. Genthner, M. Panella, and S. Rich. 1998. Reduction in pulmonary vascular resistance with long-term epoprostenol (prostacyclin) therapy in primary pulmonary hypertension. *N Engl J Med* 338:273-7.

9) Rubin L J, Badesch D B, Barst R J, Galie N, Balck C M, Keogh A, Pulido T, Frost A, roux S, Leconte I, Landzberg M, Simonneau G. 2002, Bosentan therapy for pulmonary arterial hypertension. *N Engl J Med* 346: 896-903.

10) Jones, D., C. Benjamin, and D. Linseman. 1995. Activation of thromboxane and prostacyclin receptors elicits opposing effects on vascular smooth muscle cell growth and mitogen-activated protein kinase signaling cascades. *Mol Pharm* 48:890-89.

11) Langleben, D., Brock, T., Dixon, R., and Barst, R. 2004. STRIDE 1: Effects of the Selective ETA Receptor Antagonist, Sitaxsentan Sodium, in a Patient Population with Pulmonary Arterial Hypertension that meets Traditional Inclusion Criteria of Previous Pulmonary Arterial Hypertension Trials. *J Cardiovasc Pharmacol* 44:S80-S84.9)

12) Lee, A. J., Chiao, T. B., and Tsang, M. P. 2005. Sildenafil for pulmonary hypertension. *Ann Pharmacother* 39:869-884.

13) Kataoka, M., Satoh, T., Manabe, T., Anzai, T., Yoshikawa, T., Mitamura, H., and Ogawa, S. 2005. Oral sildenafil improves primary pulmonary hypertension refractory to epoprostenol. *Circ J* 69:461-465.

14) Oudiz, R. J., Schilz, R. J., Barst, R. J., Galie, N., Rich, S., Rubin, L. J., and Simonneau, G. 2004. Treprostinil, a prostacyclin analogue, in pulmonary arterial hypertension associated with connective tissue disease. *Chest* 126:420-427.

15) Vachiery, J. L., and Naeije, R. 2004. Treprostinil for pulmonary hypertension. *Expert Rev Cardiovasc Ther* 2:183-191.

16) Galie, N., Manes, A., and Branzi, A. 2002. The new clinical trials on pharmacological treatment in pulmonary arterial hypertension. *Eur Respir J* 20:1037-1049.

17) Prie, S., Stewart, D. J., and Dupuis, J. 1998. EndothelinA receptor blockade improves nitric oxide-mediated vasodilation in monocrotaline-induced pulmonary hypertension. *Circulation* 97:2169-2174.

18) Prie, S., Leung, T. K., Cernacek, P., Ryan, J. W., and Dupuis, J. 1997. The orally active ET(A) receptor antagonist (+)-(S)-2-(4,6-dimethoxy-pyrimidin-2-yloxy)-3-methoxy-3,3-diphenyl-propionic acid (LU 135252) prevents the development of pulmonary hypertension and endothelial metabolic dysfunction in monocrotaline-treated rats. *J Pharmacol Exp Ther* 282:1312-1318.

19) Jasmin, J. F., Lucas, M., Cernacek, P., and Dupuis, J. 2001. Effectiveness of a nonselective ET(A/B) and a selective ET(A) antagonist in rats with monocrotaline-induced pulmonary hypertension. *Circulation* 103:314-318.

20) Yuyama, H., Fujimori, A., Sanagi, M., Koakutsu, A., Sudoh, K., Sasamata, M., and Miyata, K. 2004. The orally active nonpeptide selective endothelin ETA receptor antagonist YM598 prevents and reverses the development of pulmonary hypertension in monocrotaline-treated rats. *Eur J Pharmacol* 496:129-139.

21) Hill, N. S., Warburton, R. R., Pietras, L., and Klinger, J. R. 1997. Nonspecific endothelin-receptor antagonist blunts monocrotaline-induced pulmonary hypertension in rats. *J Appl Physiol* 83:1209-1215.

22) Itoh, T., Nagaya, N., Fujii, T., Iwase, T., Nakanishi, N., Hamada, K., Kangawa, K., and Kimura, H.2004. A combination of oral sildenafil and beraprost ameliorates pulmonary hypertension in rats. *Am J Respir Crit. Care Med* 169:34-38.

23) Schermuly, R. T., Kreisselmeier, K. P., Ghofrani, H. A., Samidurai, A., Pullamsetti, S., Weissmann, N., Schudt, C., Ermert, L., Seeger, W., and Grimminger, F. 2004. Antiremodeling effects of iloprost and the dual-selective phosphodiesterase 3/4 inhibitor tolafentrine in chronic experimental pulmonary hypertension. *Circ Res* 94:1101-1108.

24) Abe, K., Shimokawa, H., Morikawa, K., Uwatoku, T., Oi, K., Matsumoto, Y., Hattori, T., Nakashima, Y., Kaibuchi, K., Sueishi, K., et al. 2004. Long-term treatment with a Rho-kinase inhibitor improves monocrotaline-induced fatal pulmonary hypertension in rats. *Circ Res* 94:385-393.

25) Lu, J., Shimpo, H., Shimamoto, A., Chong, A. J., Hampton, C. R., Spring, D. J., Yada, M., Takao, M., Onoda, K., Yada, I., et al. 2004. Specific inhibition of p38 mitogen-activated protein kinase with FR167653 attenuates vascular proliferation in monocrotaline-induced pulmonary hypertension in rats. *J Thorac Cardiovasc Surg* 128:850-859.

26) Schermuly, R. T., Dony, E., Ghofrani, H. A., Pullamsetti, S., Savai, R., Roth, M., Sydykov, A., Lai, Y. J., Weissmann, N., Seeger, W., et al. 2005. Reversal of experimental pulmonary hypertension by PDGF inhibition. *J Clin Invest* 115:2811-2821.

27) Mathew, R., Huang, J., Shah, M., Patel, K., Gewitz, M., and Sehgal, P. B. 2004. Disruption of endothelial-cell caveolin-1alpha/raft scaffolding during development of monocrotaline-induced pulmonary hypertension. *Circulation* 110:1499-1506.

28) Packer, M. 1985. Vasodilator therapy for primary pulmonary hypertension. Limitations and hazards. *Ann Intern Med* 103:258-270.

29) Rich S., Kaufmann E, Levy P. 1992. The effects of high doses of calcium-channel blockers on survival in primary pulmonary hypertension. *N Engl J. Med.* 327: 76-81.
30) Badesch, D. B., Abman, S. H., Ahearn, G. S., Barst, R. J., McCrory, D. C., Simonneau, G., and McLaughlin, V. V. 2004. Medical therapy for pulmonary arterial hypertension: ACCP evidence-based clinical practice guidelines. *Chest* 126:35 S-62S.
31) Badesch, D. B., Tapson, V. F., McGoon, M. D., Brundage, B. H., Rubin, L. J., Wigley, F. M., Rich, S., Barst, R. J., Barrett, P. S., Kral, K. M., et al. 2000. Continuous intravenous epoprostenol for pulmonary hypertension due to the scleroderma spectrum of disease. A randomized, controlled trial. *Ann Intern Med* 132:425-434.
32) Humbert, M., Sanchez, O., Fartoukh, M., Jagot, J. L., Le Gall, C., Sitbon, O., Parent, F., and Simonneau, G. 1999. Short-term and long-term epoprostenol (prostacyclin) therapy in pulmonary hypertension secondary to connective tissue diseases: results of a pilot study. *Eur Respir J* 13:1351-1356.
33) Robbins, I. M., Gaine, S. P., Schilz, R., Tapson, V. F., Rubin, L. J., and Loyd, J. E. 2000. Epoprostenol for treatment of pulmonary hypertension in patients with systemic lupus erythematosus. *Chest* 117:14-18.
34) Aguilar, R. V., and Farber, H. W. 2000. Epoprostenol (prostacyclin) therapy in HIV-associated pulmonary hypertension. *Am J Respir Crit. Care Med* 162:1846-1850.
35) Rosenzweig, E. B., Kerstein, D., and Barst, R. J. 1999. Long-term prostacyclin for pulmonary hypertension with associated congenital heart defects. *Circulation* 99:1858-1865.
36) Archer, S. L., Djaballah, K., Humbert, M., Weir, K. E., Fartoukh, M., Dall'ava-Santucci, J., Mercier, J. C., Simonneau, G., and Dinh-Xuan, A. T. 1998. Nitric oxide deficiency in fenfluramine- and dexfenfluramine-induced pulmonary hypertension. *Am J Respir Crit. Care Med* 158: 1061-1067.
37) Reeve, H. L., Nelson, D. P., Archer, S. L., and Weir, E. K. 1999. Effects of fluoxetine, phentermine, and venlafaxine on pulmonary arterial pressure and electrophysiology. *Am J Physiol* 276:L213-219.
38) Nagaya, N., Shimizu, Y., Satoh, T., Oya, H., Uematsu, M., Kyotani, S., Sakamaki, F., Sato, N., Nakanishi, N., and Miyatake, K. 2002. Oral beraprost sodium improves exercise capacity and ventilatory efficiency in patients with primary or thromboembolic pulmonary hypertension. *Heart* 87:340-345.
39) Hoeper, M. M., Niedermeyer, J., Hoffmeyer, F., Flemming, P., and Fabel, H.1999. Pulmonary hypertension after splenectomy? Ann Intern Med 130:506-509.
40) Hoeper, M. M., Halank, M., Marx, C., Hoeffken, G., Seyfarth, H. J., Schauer, J., Niedermeyer, J., and Winkler, J. 2005. Bosentan therapy for portopulmonary hypertension. Eur Respir J 25:502-508.

All references cited and/or discussed in this specification are incorporated herein by reference in their entirety and to the same extent as if each reference was individually incorporated by reference.

What is claimed is:

1. A method of treating class I pulmonary hypertension (pulmonary arterial hypertension (PAH)), comprising administering a therapeutically effective amount of a selective JAK2 inhibitor to a patient in need thereof.
2. The method of claim 1, wherein the selective JAK2 inhibitor is a tyrphostin.
3. The method of claim 2, wherein the tyrphostin is AG490.
4. The method of claim 1, wherein the patient is a human.
5. The method of claim 1, wherein the JAK2 inhibitor is administered in a total daily dosage of about 3 mg/kg/day.
6. A method of reducing the occurrence of pulmonary arteriolar obstruction in a patient afflicted with class I pulmonary hypertension, comprising administering an effective amount of a selective JAK2 inhibitor to the patient.
7. The method of claim 6, wherein the JAK2 inhibitor is a tyrphostin.
8. The method of claim 7, wherein the tyrphostin is AG490.
9. The method of claim 6, wherein the patient is a human.
10. The method of claim 6, wherein the JAK2 inhibitor is administered in a total daily dosage of about 3 mg/kg/day.
11. The method of claim 6, wherein the JAK2 inhibitor is administered orally, by inhalation, intravenously, subcutaneously, transdermally, or intraperitoneally.
12. The method of claim 1, wherein the selective inhibitor of JAK2 inhibits JAK2 activity at least 2-fold more than it inhibits JAK1, JAK3 or TYK2 activity.
13. The method of claim 1, wherein the selective inhibitor of JAK2 inhibits JAK2 activity at least 5-fold more than it inhibits JAK1, JAK3 or TYK2 activity.
14. The method of claim 1, wherein the selective inhibitor of JAK2 inhibits JAK2 activity at least 10-fold more than it inhibits JAK1, JAK3 or TYK2 activity.
15. The method of claim 1, wherein the JAK2 inhibitor is contained within or attached to an implant.
16. The method of claim 1, wherein the pulmonary arterial hypertension is associated with hereditary hemorrhagic telangiectasia, congenital heart disease, familial primary pulmonary hypertension, idiopathic pulmonary arterial hypertension, splenectomy, HIV infection, a collagen vascular disorder, scleroderma, mixed connective tissue disease, systemic lupus erythematosus, chronic thromboembolic pulmonary artery hypertension (distal or inoperable), toxins, anorexigens, liver disease, liver disease caused by hepatitis C or liver disease associated with portal hypertension.
17. The method of claim 6, wherein the JAK2 inhibitor inhibits JAK2 activity at least 2-fold more than it inhibits JAK1, JAK3 or TYK2 activity.
18. The method of claim 6, wherein the JAK2 inhibitor inhibits JAK2 activity at least 5-fold more than it inhibits JAK1, JAK3 or TYK2 activity.
19. The method of claim 6, wherein the JAK2 inhibitor inhibits JAK2 activity at least 10-fold more than it inhibits JAK1, JAK3 or TYK2 activity.
20. The method of claim 6 wherein the JAK2 inhibitor is contained within or attached to an implant.

* * * * *